(12) United States Patent
Rakshit (10) Patent No.: US 11,621,068 B2
(45) Date of Patent: Apr. 4, 2023

(54) ROBOTIC ARM FOR PATIENT PROTECTION

(71) Applicant: International Business Machines Corporation, Armonk, NY (US)

(72) Inventor: Sarbajit K. Rakshit, Kolkata (IN)

(73) Assignee: International Business Machines Corporation, Armonk, NY (US)

( * ) Notice: Subject to any disclaimer, the term of this patent is extended or adjusted under 35 U.S.C. 154(b) by 251 days.

(21) Appl. No.: 17/017,795

(22) Filed: Sep. 11, 2020

(65) Prior Publication Data

US 2022/0084650 A1 Mar. 17, 2022

(51) Int. Cl.
| | | |
|---|---|---|
| G16H 20/30 | (2018.01) | |
| G06F 1/16 | (2006.01) | |
| G06T 19/00 | (2011.01) | |

(52) U.S. Cl.
CPC ............. *G16H 20/30* (2018.01); *G06F 1/163* (2013.01); *G06T 19/006* (2013.01)

(58) Field of Classification Search
CPC ........ G16H 20/30; G06F 1/163; G06T 19/006
See application file for complete search history.

(56) References Cited

U.S. PATENT DOCUMENTS

| | | | |
|---|---|---|---|
| 9,254,216 B2 | 2/2016 | Limonadi | |
| 10,013,062 B1 | 7/2018 | Corson | |
| 11,270,576 B2 * | 3/2022 | Franz | G08B 21/0469 |
| 2010/0217163 A1 * | 8/2010 | Sankai | B25J 9/0006 |
| | | | 601/5 |
| 2012/0142416 A1 * | 6/2012 | Joutras | A63F 13/285 |
| | | | 463/36 |
| 2013/0198625 A1 * | 8/2013 | Anderson | G06F 3/016 |
| | | | 715/701 |
| 2016/0313798 A1 * | 10/2016 | Connor | G06F 3/017 |
| 2017/0143261 A1 * | 5/2017 | Wiedenhoefer | A61B 5/0086 |
| 2018/0110669 A1 * | 4/2018 | Rodriguez Leal | A61H 1/0281 |
| 2018/0232593 A1 * | 8/2018 | Tani | G06V 10/22 |
| 2019/0206134 A1 * | 7/2019 | Devam | G06T 19/00 |

(Continued)

OTHER PUBLICATIONS

Johnson, Dave, "How a Fitbit is able to accurately track your sleep, and how to check your sleep stats", Business Insider, India, Aug. 30, 2019, 5 Pages.

(Continued)

*Primary Examiner* — Haoshian Shih
(74) *Attorney, Agent, or Firm* — Edward J. Wixted, III (57) ABSTRACT

An approach for a computer in a robotic arm device attached to a patient to receive data identifying at least one protected area of the patient from a computing device of a medical professional. The approach includes the computer receiving instructions for one or more actions by the robotic arm device associated with the least one protected area of the patient from the computing device of the medical professional. Additionally, the approach includes the computer receiving sensor data associated with one or more movements of the patient from one or more sensors in the robotic arm device and determining that a hand of the patient in the robotic arm device is entering the at least one protected area. Furthermore, the approach includes the computer initiating one action of one or more actions by the robotic arm device that is associated with the least one protected area of the patient.

18 Claims, 7 Drawing Sheets

(56) References Cited

U.S. PATENT DOCUMENTS

| | | | | |
|---|---|---|---|---|
| 2020/0029635 | A1* | 1/2020 | Kiemele | A41D 19/015 |
| 2021/0285633 | A1* | 9/2021 | Esmailzadeh | A61L 2/10 |
| 2021/0322869 | A1* | 10/2021 | Knoppert | G02B 27/017 |
| 2021/0370496 | A1* | 12/2021 | Stuart | G16H 40/67 |
| 2022/0040008 | A1* | 2/2022 | Ho | A61F 13/36 |
| 2022/0167879 | A1* | 6/2022 | Wu | G16H 20/30 |
| 2022/0175558 | A1* | 6/2022 | Jarrassé | A61H 1/0277 |

OTHER PUBLICATIONS

Zubrycki et al., "Novel Haptic Device using Jamming Principle for Providing Kinaesthetic Feedback in Glove-Based Control Interface", J Intell Robot Syst (2017), 85:413-429, DOI 10.1007/s10846-016-0392-6, Published online: Jun. 15, 2016, 17 Pages.

* cited by examiner

FIG. 7

ROBOTIC ARM FOR PATIENT PROTECTION

BACKGROUND

The present invention relates generally to the field of computer assisted medical devices, and more particularly to a robotic arm device utilizing integrated computer processors, sensors, and a computer program to protect a person from contacting medically identified areas of their body.

In some patient situations, particularly post-surgery, it is desirable that various tubes, surgical locations, or body parts are not touched by the patient in order to prevent the patient from accidentally dislodging or moving a medical device or to prevent the patient from contaminating specific surgical areas or surgical stitches. Typically, physicians or nurses provide verbal instructions directing a patient not to contact post-surgical sites to allow effective post-surgery patient healing. Patients are often reminded by nurses, doctors, or another hospital staff assigned to a patient during rounds and at other times during a patient's hospital stay not to touch specific areas such as wound sites or not remove an IV tube. Commonly, after a surgical repair of a joint, digit, limb, or other body part, a patient's movement of the surgically repaired area should be minimized. It is also important that during a post-surgical hospital stay that the patient does not cause infections to wounds or illness by touching a nose, a mouth, eyes, or a surgical site. Generally, nurses, doctors or other appropriate hospital staff may periodically, during rounds, monitor a patient's compliance with the provided directions on limited contact with identified areas such as the surgically repaired area or, in some cases, to observe if the patient is following instructions on limited movement of surgical areas like an arm, an elbow, or a shoulder.

SUMMARY

Embodiments of the present provide a method, a computer program product, a computer system, and robotic arm device attached to a patient where the method includes, one or more computer processors, receiving data identifying at least one protected area of the patient from a computing device of a medical professional. The method includes the computer processors receiving, from the computing device of the medical professional, instructions for one or more actions by the robotic arm device associated with the least one protected area of the patient. Additionally, the method includes the computer processors receiving sensor data associated with one or more movements of the patient from one or more sensors in the robotic arm device and determining that a hand of the patient in the robotic arm device is entering the at least one protected area. Furthermore, the method includes the computer processors initiating an action of the one or more actions by the robotic arm device associated with the least one protected area of the patient.

DETAILED DESCRIPTION

Embodiments of the present invention recognize that an ability to provide a patient with computer-enabled robotic device that can protect a patient from inadvertently touching a critical post-surgical area or accidentally dislodging an important medical device would be advantageous to help with the recovery of the patient. Post-surgical patients can require intravenous tube connections for medicine, masks for oxygen, connections for heart rate monitors, joint repairs requiring limited joint movement post-surgery, and the post-surgical patient can have surgical stich areas that should be protected from contact by the patient. Additionally, embodiments of the present invention recognize that a patient can inadvertently transfer or introduce viruses, bacteria, and other harmful pathogens to a critical area of the patient such as a face, a stitch area, or a wound area when the unclean hands of the patient contact a critical area. The inadvertent introduction of a pathogen into a critical area can cause infection or illness in the patient. Embodiments of the present invention recognize that a sleeping, anesthetized, or heavily medicated patient could inadvertently contact stitches, dislodge an oxygen mask or intravenous (IV) tube by hand, arm, or finger movements in addition to accidentally introducing pathogens to a surgical area or facial area with unclean hands during sleep or recovery from anesthesia. Embodiments of the present invention recognize that a method of protecting critical areas of a post-surgical patient to prevent a patient from removing attached medical devices or from infecting themselves due to uncleansed hands would promote patient recovery.

Additionally, embodiments of the present invention recognize that a computer program and device that could learn patient specific motions that proceed a patient's arm or hand entry into a critical area such as an IV tube connection or contacting a face mask for oxygen in order to learn the patient's movements that typically proceed entry into one of the critical areas. Embodiments of the present invention recognize that a program that can learn the patient's movements, monitor the patient's movements, includes instructions warn the patient of a movement into a critical area or includes instructions to restrict the patient's movement into a critical area can prevent the patient from contacting a critical area. The protection of critical patient areas would be helpful in aiding hospital staff in preventing the patient from accidental self-injury or patient contamination of critical post-surgical areas.

Embodiments of the present invention further recognize that a device preventing a child, an infant, or an at risk person from accidentally contacting their face, eyes, or mouth with uncleansed hands would be helpful in reducing transmission of viruses, bacterial, or other pathogens transferred by touch. Embodiments of the present invention recognize that an ability to provide a method of dis-infecting a patient's prior to contacting one of these patient critical areas to prevent infection or disease spread is also desirable.

Embodiments of the present invention provide a robotic arm device with a number of sensors including digital cameras, controllers, mechanical bracing, hinging mechanisms, and a computer program that attaches to the patient's arm and wrist to monitor a patient's movements. Embodiments of the present invention provide the robotic device with various computer processors and a computer program that can learn the patient's movements and be programmed with medically directed actions. Embodiments of the present invention provide a robotic arm device that provides an audible alert and/or resistance to entry into a protected area of the patient.

Embodiments of the present invention provide a method, a computer program, a computer system, and a robotic arm device allow a patient in a hospital bed to move their hands and arms as desired by the patient while preventing the patient from touching critical areas including oxygen face mask, IV tubes, surgical areas, and the patient's mouth, nose, or eyes.

Embodiments of the present invention provide a method of de-contaminating the patient's hands before touching one of these critical areas. Embodiments of the present invention provide a method of preventing the patient from accidentally dislodging or moving a critical medical device such as an oxygen mask or IV tube connection. The method include one or more of the following actions: alerting the patient when their hands or arms are potentially entering a patient critical area such as a stitch area, restricting the patient's movements into one of the patient critical areas, or sanitizing the patient's hand before the patient touches a critical area. Embodiments of the present invention include receiving data identifying one or more patient protected areas from a medical professional who is using augmented reality glasses to provide the identification of the critical or protected areas on the patient. The medical professionals can update or change the information on protected areas of the patient at any time as the patient progresses in the recovery process. Embodiments of the present invention include receiving from the medical professional one or more instructions for actions to be performed by the robotic arm device when the computer device in the robotic arm device determines that the patient is moving an arm, hand, or fingers into a critical, protected area such as an oxygen face mask, stitches, or the patient's facial area.

Embodiments of the present invention provide a method of identifying movements of the patient using one or more sensors in the robotic arm device. Using sensor data and machine learning algorithms, the method includes the program learning to determine the patient movements that generally proceed entry into a patient critical or protected area including one or more of the patient's face, a stitch area, or a medical device required by the patient. Embodiments of the present invention are not limited to use with patients within a hospital setting. Embodiments of the present invention are applicable, especially in times of a pandemic, to provide a method of ensuring that children, infants, Alzheimer's patients, an at-risk person, or any other person does not accidentally self-infect themselves by contacting their mouth area, eyes, or nose area with an unclean hand or fingers.

The present invention will now be described in detail with reference to the Figures.

Figure 1:
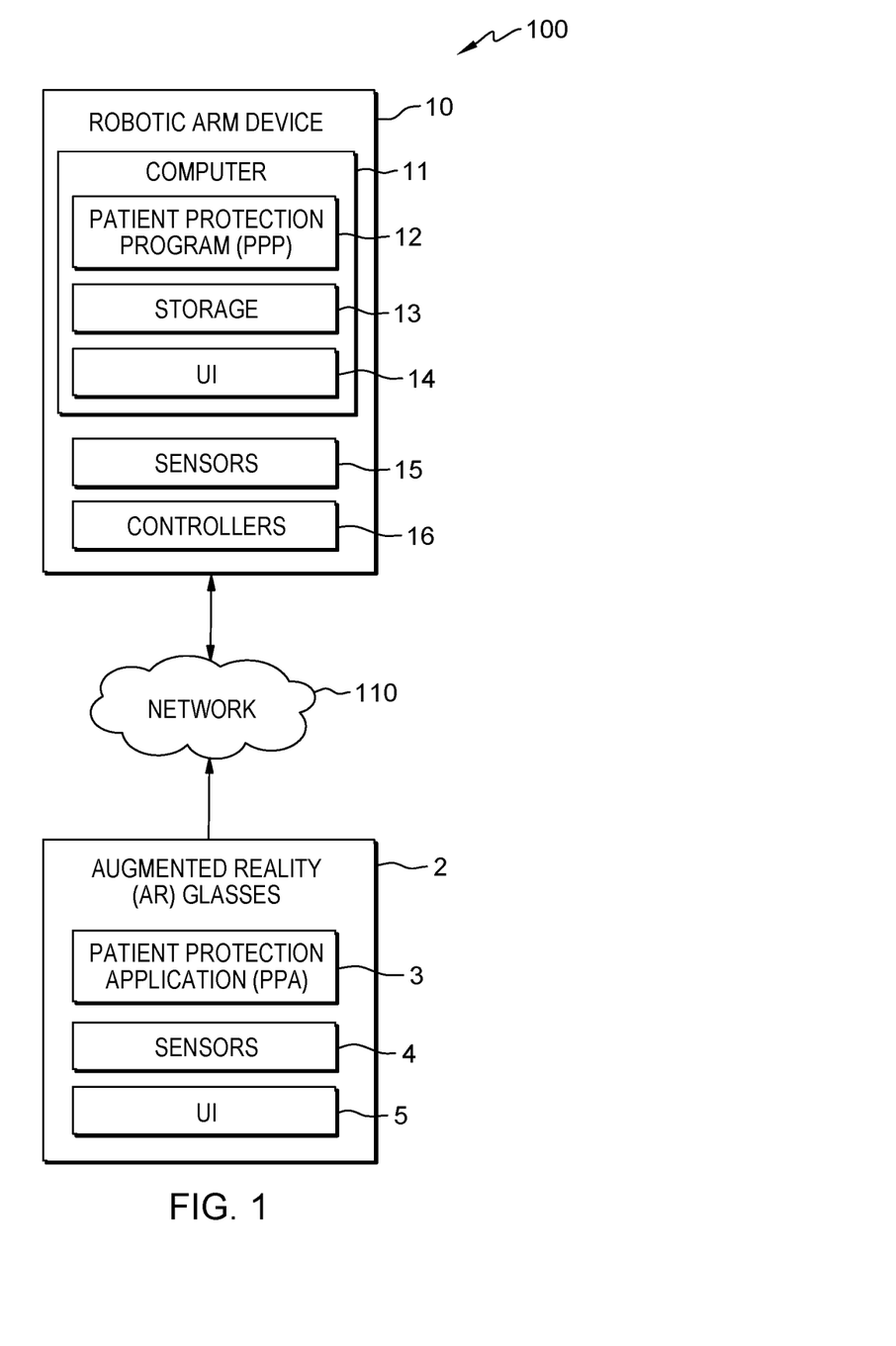
FIG. 1 depicts a functional block diagram of a computing environment suitable for operation of a patient protective program in a robotic arm device, in accordance with at least one embodiment of the invention.

FIG. 1 is a functional block diagram of a computing environment 100 suitable for operation of patient protection program (PPP) 12 in robotic arm device 10, in accordance with at least one embodiment of the invention. FIG. 1 provides only an illustration of one implementation and does not imply any limitations with regard to the environments in which different embodiments may be implemented. Implementation of embodiments of the invention may take a variety of forms, and exemplary implementation details are discussed subsequently with reference to the Figures. Many modifications to the depicted environment may be made by those skilled in the art without departing from the scope of the invention as recited by the claims.

Computing environment 100 includes robotic arm device 10 and augmented reality (AR) glasses 2 connected over network 110. In some embodiments, computer environment 100 includes a patient monitor and a cleaning station that are not depicted in FIG. 1. Network 110 can be, for example, a local area network (LAN), a wide area network (WAN), such as the Internet, a virtual local area network (VLAN), or any combination that can include wired, wireless, or optical connections. In general, network 110 can be any combination of connections and protocols that will support communications between robotic arm device 10 and augmented reality (AR) glasses 2 and any other computing devices not depicted in FIG. 1.

Figure 2:
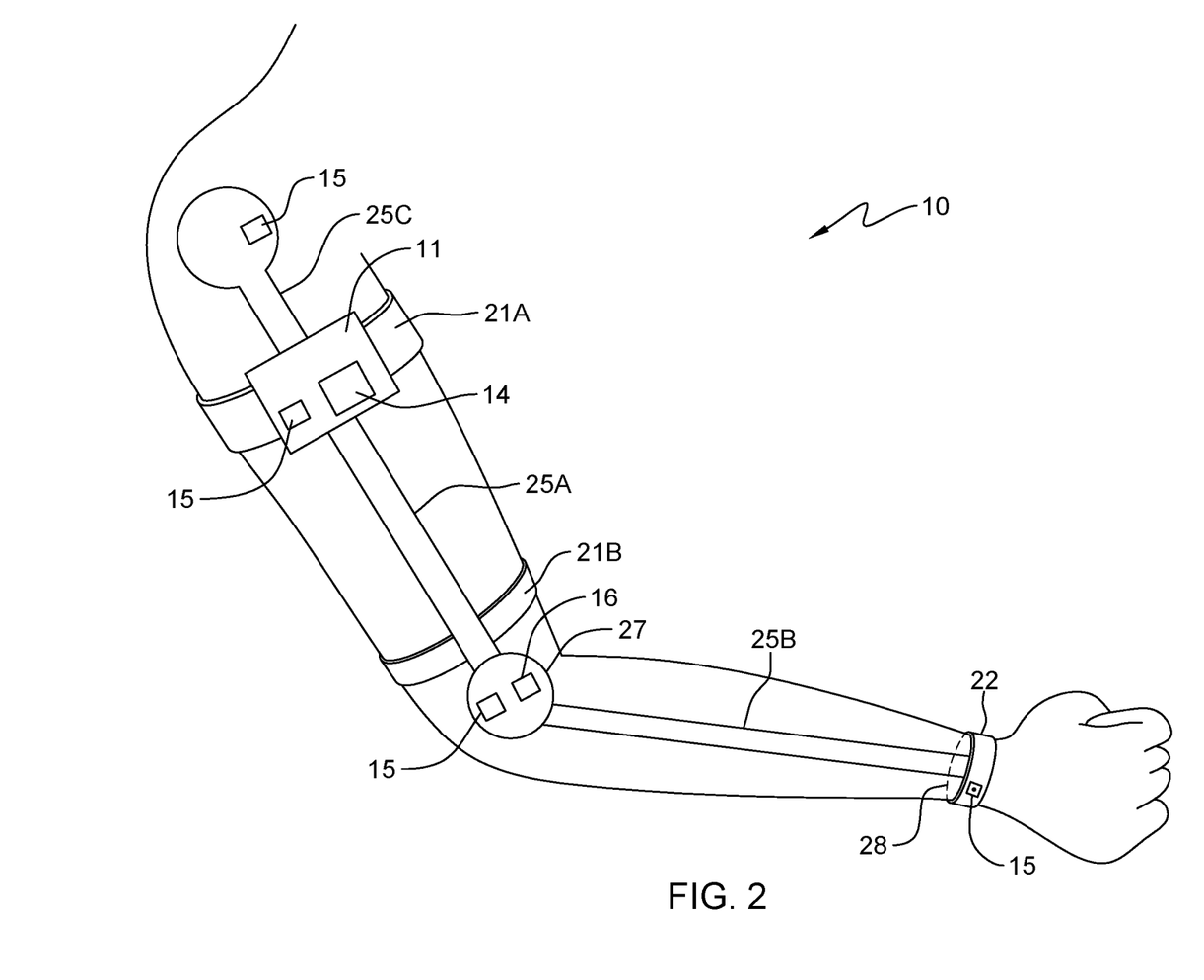
FIG. 2 is an example of an illustration of the robotic arm device with the patient protective program, in accordance with at least one embodiment of the invention.
Figure 3:
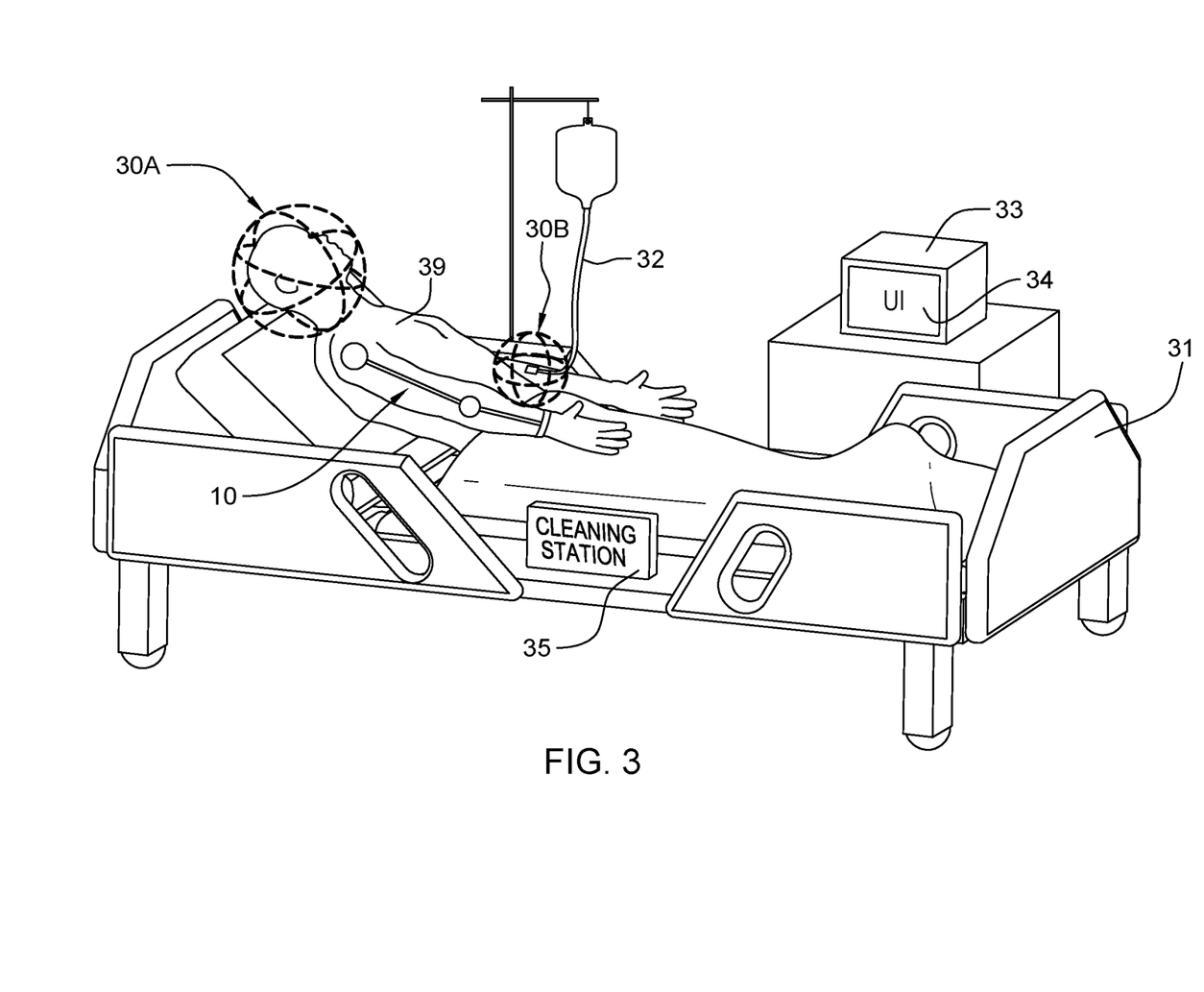
FIG. 3 is an example of an illustration of a patient using the robotic arm device in a hospital bed, in accordance with at least one embodiment of the invention.

As depicted, robotic arm device 10 includes computer 11, sensors 15, and controller 16. In various embodiments, robotic arm device 10 includes a number of other mechanical devices, such as, mechanical bracing, hinging elements and electrical devices, such as embedded controllers, wires, cables, servo motors, and resistors not depicted in FIG. 1 however, the mechanical and electrical devices are not limited to these devices and/or mechanical parts. Examples of robotic arm device 10 are depicted in FIG. 2 and FIG. 3. In various embodiments, robotic arm device 10 is attached to the patient's arm, shoulder, wrist, and fingers. In some embodiments, robotic arm device 10 is integrated into the patient's hospital gown. In an embodiment, robotic arm device 10 is integrated into a shirt or a jacket worn by a person such as a child.

Computer 11 can be one or more computer processors in one or more semiconductor devices or chips, a wearable computing device, a mobile computing device, a desktop computer system, a laptop computer, a computer system in the patient monitor, or any other programmable electronic computing device capable of executing patient protection program 12, receiving, sending, processing data, and communicating with features including sensors 15 and mechanical functions of robotic arm device 10, AR glasses 2, and any other computing devices not shown within computing environment 100 via network 110. Computer 11 may include internal and external hardware components, as depicted in more detail and described in FIG. 7. In various embodiments, computer 11 in robotic arm device 10 includes patient protection program (PPP) 12, storage 13, and user interface (UI) 14.

PPP 12 is depicted as executing in computer 11 of robotic arm device 10. In various embodiments, PPP 12 receives data identifying protected areas of a patient from AR glasses 2 worn by a medical staff assigned to treat the patient or from another computing device (not depicted) accessed by the treating medical professional. Protected areas associated with the patient may include one or more of the patient's oxygen face mask, IV tube, other required medical devices, post-surgical stitch area, facial area including the patient's nose, mouth, or eyes, surgically repaired joints, or another area associated with or near the patient that is identified by a treating medical professional as a protected area with restrictions to contact by the patient. In some embodiments, a protected area is a joint or a bone identified by the treating medical professional as requiring limited motion or contact.

In various embodiments, PPP 12 receives instructions, from AR glasses 2 or another device of the treating medical professional, for robotic arm device 10 to perform one or more actions when PPP 12 determines that the patient is moving a hand, arm, shoulder, or fingers into a protected area. For example, the instructions received by PPP 12 may include providing increasing resistance to certain movements to limit or restrict patient contact to post-surgical stitch areas. In other examples, the instructions received by PPP 12 and provided to robotic arm device 10 may be an instruction for robotic arm device 10 to move a joint to or instructions from PPP 12 provided to robotic arm device 10 for robotic arm device 10 to indicate or alert the patient of a need to perform a specified action such as to move a joint using an audible command from UI 14 in robotic arm device 10. In other cases, robotic arm device 10 may receive from PPP 12 instructions for robotic arm device 10 to indicate with a sound or a verbal command from UI 12 a patient's need to sanitize their hands prior to touching a protected area, such as, their face or the IV tube connection.

In various embodiments, PPP 12 receives and analyzes data on one or more of the patient's arm movements, shoulder movements, finger movements, and hand movements received from sensors 15 and controller 16. PPP 12 sends and receives data and instructions to and from controller 16 on robotic arm device 10 movements. PPP 12 analyzes the sensor data such as video data and determines when the patient's hand, fingers, or arm is entering a protected area. In various embodiments, PPP 12 includes machine learning algorithms capable of analyzing received sensor data of the patient's movements. PPP 12 learns from historical patient movements the patient the patient's movement most likely to initiate the entry of the patient's hand, arm, or fingers into a protected area of the patient. In some embodiments, PPP 12, in response to determining that the patient's movements indicate a desire to touch a protected area or probable entry into a protected area, PPP 12 sends instructions to robotic arm device 10 to disinfect or clean the patient's hands.

In some embodiments, PPP 12 executes on the patient monitor (not depicted in FIG. 1). In this embodiment, the patient monitor with one or more computer processors receives data identifying the patient's protected areas from one of AR glasses 2, from another computer device or tablet of the medical staff, or from a user interface on the patient's monitor. The medical staff associated with the patient's care can provide location data for one or more protected areas received by AR glasses 2. In other embodiments, the medical staff provide protected area locations that received by touch on the patient monitor user interface or received verbally by the patient's monitor and sent to PPP 12. In some embodiments, PPP 12 operates on computer 11 in robotic arm device 10 and provides data on the patient's movements over network 110 to a hospital computer system or a server (not depicted in FIG. 1) that is available to authorized hospital staff. PPP 12 may receive and send data to and from computer 11, sensors 15, controller 16, AR glasses 2, and any other computer devices not depicted within computing environment 100 using network 110.

Storage 13 is depicted in computer 11. Storage 13 may be any known type of storage and may include one or more databases. Storage 13 may store and/or retrieve received data from AR glasses 2 including identification of protected areas, sensor data from sensors 15, retrieve or store instructions and data to and from controller 16 and any data received from controller 16, AR glasses 2, PPP 12, sensors 15, controllers 16, or another computing device not depicted in FIG. 1.

UI 14, depicted in computer 11, provides a user interface for a user to access the features and functions of computer 11 and robotic arm device 10. UI 14 provides an ability for a user to interaction with computer 11 to display output or data to the user and/or receive user input of instructions to computer 11. UI 14 may be any type of known user interface capable of receiving a user's input and/or displaying data or output. For example, UI 14 may be a touch screen display, a very small keyboard, an audio device, an alarm, a user interface with a voice recognition system, etc. UI 14 can provide a user an ability to interact with computer 11 and PPP 12 in robotic arm device 10.

Sensors 15 are depicted in robotic arm device 10. Any number of sensors 15 may be present in various locations of robotic arm device 10. Sensors 15 may include but, are not limited to, motion sensors, accelerometers, digital video cameras, microelectromechanical system (MEMS) gyroscopes, radio frequency (RF) devices, biometric sensors, and compass chips for gathering data related to patient's hand, arm, shoulder, and finger movements. Sensors 15 collect data associated with a movement of the patient's hand, fingers, thumb, shoulder, or arm including speed, acceleration, direction, and muscle movement with biometric sensors or piezoelectric sensors that is sent to computer 11. In some cases, sensors 15 (e.g., biometric sensors for muscle movements or temperature) may be directly attached to the patient and communicate wirelessly with computer 11 in robotic arm device 10. Sensors 15 may reside on various locations of robotic arm device 10 including but, not limited to, locations on robotic arm device 10 associated with the patient's shoulder, arm, elbow, wrist, and in some cases, locations on finger extensions of robotic arm device 10. In various embodiments, finger extensions to robotic arm device 10 are on one or more extensions of robotic arm device 10 connecting to each of the patient's fingers and include video recording capability (not depicted).

In some embodiments, sensors 15 include near-field communication (NFC) devices that are radio frequency (RF) devices capable of sending and receiving wireless data, such as a proximity and/or location data to and from another NFC device which may be attached to the patient, or the patient's medical equipment or bed. Sensors 15 can send NFC communication data to computer 11. In some cases, sensors 15 can include range finder sensors capable of determining distance to objects, such as, a distance to an IV tube. In other embodiments, sensors 15 are sleep detection sensors. Using known activity tracker technology to determine sleep status, sensors 15 can provide information to PPP 12 on when a patient is sleeping. In some embodiments, based on sensors 15 detecting that the patient is asleep, using, PPP 12 uses a different set of instructions regarding patient protected areas than the instructions to robotic arm device 10 when the patient is awake. Sensors 15 can be any type of sensor capable of collecting and providing information regarding one or more movements of a patient's arm, shoulder, fingers, thumb, or hand and joints associated with these patient areas.

Controller 16 depicted in robotic arm device 10 may be one or more controllers, such as an embedded controller or the like, capable of sending data to PPP 12, receiving instructions from PPP 12 and executing the instructions from PPP 12. For example, controller 16 can receive from PPP 12 instructions to increase resistance to arm movement or instructions to lock a hinging device or ball joint in robotic arm 10 to prevent patient movement into a protected area (e.g., a recent surgical repair area). Controller 16 can send and receive data associated with the patient's movement. For example, controller 16 can send data related to the amount of energy or power used to prevent or cause a patient movement. Controller 16 can be any type of known controller, processor, or other semiconductor device capable of executing instructions from PPP 12 in robotic arm device 10 in order to control, direct, determine, or alter the movement of the patient's hand, arm, or shoulder using robotic arm device 10 and controller 16.

AR glasses 2 may be a computing device using an augmented reality display, a wearable computer, a laptop computer, a tablet computer, a smart phone, or any programmable electronic device capable of communicating with robotic arm device 10 via network 110 and any other computing devices not depicted in computer environment 100. In various embodiments, AR glasses 120 are a wearable, augmented reality computing device. In various embodiments, AR glasses 2 are user worn glasses providing a virtual reality screen or display to the user. In general, AR glasses 2 represent a programmable electronic device, a computing device or a combination of programmable computer chips and electronic devices capable of executing machine readable program instructions and communicating with other computing devices via a network, such as network 110. As depicted, AR glasses 2 include patient protection application (PPA) 3, sensors 4, and UI 5. AR glasses 2 can provide digital image projection used in UI 5 to display information, data and user inputs. AR glasses 2 may be capable of sending and receiving data or user provided inputs such as an identification of protected area locations on the patient. For example, a medical professional wearing AR glasses 2 may identify the protected areas, by gaze detection, by focal point detection, or a shared digital image captured using known methods by one of sensors 4 and/or UI 5 and sent to one of PPA 3 or robotic arm device 10. The data or inputs on UI 5 captured by AR glasses 2 can be sent by the medical profession to PPP 12 in robotic arm device 10 via network 110. AR glasses 2 may include internal and external hardware components, as depicted and described in further detail with respect to FIG. 7.

In various embodiments, PPA 3 is an application in AR glasses 2 that sends and receives commands and data to and from sensors 4, UI 5, computer 11 in robotic arm device 10, and other computing devices not depicted in computer environment 100. For example, PPA 3 receives gaze detection data from sensors 4 in AR glasses 2 worn by a medical professional responsible of the care of the patient. In some embodiments, PPA 3 receives digital image data such as video or still image data from sensors 4 in AR glasses 2 indicating a protected area that is sent to PPP 12 in robotic arm device 10. In various embodiments, PPA 3 receives user inputs on UI 5 using known methods of AR glass input such as gaze detection on a virtual tool bar item or the like. The inputs may indicate to PPA 3 one or more protected areas associated with the patient for transmission by PPA 3 to PPP 12 over network 110. PPA 3 sends and receives data, such as, but is not limited to patient protect area identification, to and from sensors 4 and UI 5 and robotic arm device 10.

Sensors 4 are depicted in AR glasses 2. Sensors 4 can be any type of sensors capable of integration into AR glasses 2. For example, sensors 4 may include gaze detection sensors, focal point detection sensors, digital image capture technology such as a digital camera, image scanning technology, and other capabilities sensor capabilities utilized in AR glasses. Sensor 4 in AR glasses 2 may send and receive data and/or instructions from PPA 3, UI 5, and to and from robotic arm device 10.

UI 5 is depicted in AR glasses 2. UI 5 can be any type of known user interface technology utilized in augmented reality glasses. For example, UI 5 may use gaze detection to indicate a desired action in a virtual menu displayed on UI 5 of AR glasses 2. UI 5 provides an interface for communication between a medical professional assigned to the patient who is using AR glasses 2 and any applications or programs residing in AR glasses 2. For example, UI 5 may receive an indication of a still digital image or video of a patient protected area from the medical professional. UI 5 can receive from the medical professional a command to send the still image of the patient protected area to PPA 3 and PPP 12. In various embodiments, UI 5 sends and receives commands and data to and from a user. For example, UI 5 receives from a user instructions to send data from PPA 3 captured by sensors 4 to robotic arm device 10.

FIG. 2 is an example of an illustration of robotic arm device 10, in accordance with at least one embodiment of the invention. As depicted in FIG. 2, robotic arm device 10 includes sensors 15, computer 11, UI 14, arm bands 21A and 21B, wrist band 22, arm bracing mechanisms 25A and 25B, shoulder extension 25C, controller 16, hinge 27, and ultraviolet (UV) source 28 (indicated on the back of wrist band 22 but not specifically depicted in FIG. 2). FIG. 2 is exemplary embodiment of robotic arm device 10. Variations of arm band placement, computer placement, controller placement, type of hinging devices, servo motors, mechanical bracing, etc. could be depicted in other embodiments of the present invention.

Hinge 27 can be a two directional hinge providing movement in two directions, a ball and joint type of hinge providing movement in all directions, a stretchable band, an electro-mechanically driven hinge providing mechanical motion or resistance, or any other known type of moveable joint between arm bracing mechanisms 25A and 25B capable use providing joint movement for a patient in robotic arm device 10. In various embodiments, one or more hinge 27 providing one or more moveable joints are present in robotic arm device 10 (e.g., an elbow hinge, a wrist hinge, etc.). In some embodiments, additional hinges similar to hinge 27 are present in wrist band 22 area, in an area associated with shoulder extension 25C, or other area associated with robotic arm device 10. In various embodiments, a controller, such as controller 16, can be associated with hinge 27.

UV light source 28 on the back or bottom side of wrist band 22 can be used as a cleaning device to remove germs, virus, or other surface pathogens from the patient's hand (e.g., palm, thumb, and fingers). For example, when PPP 12 determines that the patient is moving their hands into a protect area, such as, the patient's mouth, PPP 12 issues a command to UV light source to disinfect the patient's hand. In other embodiments, UV light source 28 is replaced with a spray disinfectant dispense nozzle.

In some embodiments, robotic arm device 10 includes audio devices as alarms (e.g., ringing, buzzing, or pre-recorded verbal commands) and finger extensions with digital imaging devices (e.g., camera) not depicted in FIG. 2. In other embodiments, robotic arm device 10 is integrated into a hospital gown or shirt worn by the patient (not depicted in FIG. 2).

FIG. 3 is an example of an illustration of a patient using robotic arm device 10 in hospital bed 31, in accordance with at least one embodiment of the invention. As depicted FIG. 3 includes protected area 30A and 30B, IV tube 32, patient monitor 33 with UI 34, hospital bed 31 with cleaning station 35, patient 39, and robotic arm device 10. In various embodiments, protected area 30A and 30B are 3 dimensional spaces. For example, protected area 30A or 30B can be a dome, a rectangular space, or a spherical area. As depicted in FIG. 3, protected area 30A is a spherical area around a patient's face or head and protected area 30B is an area around an IV tube patient entry area. In other embodiments, protected area 30A is a two-dimensional area (e.g., a stitch area). In an embodiment, an RF tag (not depicted) is attached to the patient, to bandages on the patient, or in the patient's hospital gown to identify protected areas 30A and 30B to sensors 15. Protected area 30A and 30B can be any shape or size of the protected area as identified by the medical professional assigned to the patient. In one embodiment, protected area 30A or 30B is a joint such as an elbow or a shoulder which should not be moved. As previously discussed, protected area 30A and 30B may be changed at any time by the medical professional assigned to the patient.

In some embodiments, cleaning station 35 is present. Cleaning station 35 may have a proximity sensor and/or a computer processor chip with a wireless connection to PPP 12 in robotic arm device 10. Cleaning station 35 can be one of a UV light source, an ultrasonic cleaner, a small tank with a disinfectant liquid, or a spray disinfectant machine. In some embodiments, PPP 12 provides verbal directions directing the patient to clean his or her hand before entering a protected area, such as, protected area 30A. In another embodiment, PPP 12 sends a command to robotic arm device 10 to provide a mechanical alert, such as a vibration or a resistance to the patient's movement toward a protected area to remind to the patient to sanitize or clean their hands in cleaning station 35. Cleaning station 35 provides decontamination of the patient's hand or hands prior to touching his or her mouth, eyes, nose, facial area, or other protected area, for example, when the patient desires to re-adjust a face mask or blow their nose. In some cases, when PPP 12 determines that the patient's hand is about to enter one of protected areas 30A or 30B, based on sensor data from one or more sensors in robotic arm device 10, PPP 12 provides an instruction to cleaning station 35 to activate the UV light source for disinfection the patient's hand and an audible alert or verbal instruction to the patient to clean their hands with cleaning station 35. Cleaning station 35 may include proximity sensors (not depicted) that automatically turn on UV lights or disinfectant spray when the patient hand, palm, thumb, or fingers enter the pre-determined cleaning space.

In one embodiment, patient 39 has patches or radio frequency (RF) tags applied by a medical professional responsible for the patient's care on the patient's body, the patient's bandages, or the patient's hospital gown on a protected area or on the hospital bed in the immediate vicinity of a protected area. In this case, one or more of the sensors in robotic arm device 10 are RF receivers or RF chips that can detect and determine a proximity to a protected area using NFC and the RF receiver. In some cases, when PPP 12 determines that the patient's hand is entering protected area 30B using received data from the RF devices (e.g., RF tags and receivers), PPP 12 sends instructions to robotic arm device 10 to provide resistance to entry into protected area 30B or prevents the patient from contacting protected area 30B by locking hinge 27.

In one embodiment, patient monitor 33 includes PPP 12. In this case, PPP 12, in patient monitor 33, receives inputs from the medical professional. For example, PPP 12 may receive digital image data from AR glasses 2 worn by the medical professional or may receive inputs received on UI 34 in patient monitor 33 regarding protected area 30A or 30B. In these embodiments, PPP 12 in patient monitor 33 can send instructions and data to and from computer 11 in robotic arm device 10. Patient monitor 33 can connect to robotic arm device 10 wirelessly or through a wired connection when PPP 12 resides in patient monitor 33.

Figure 4:
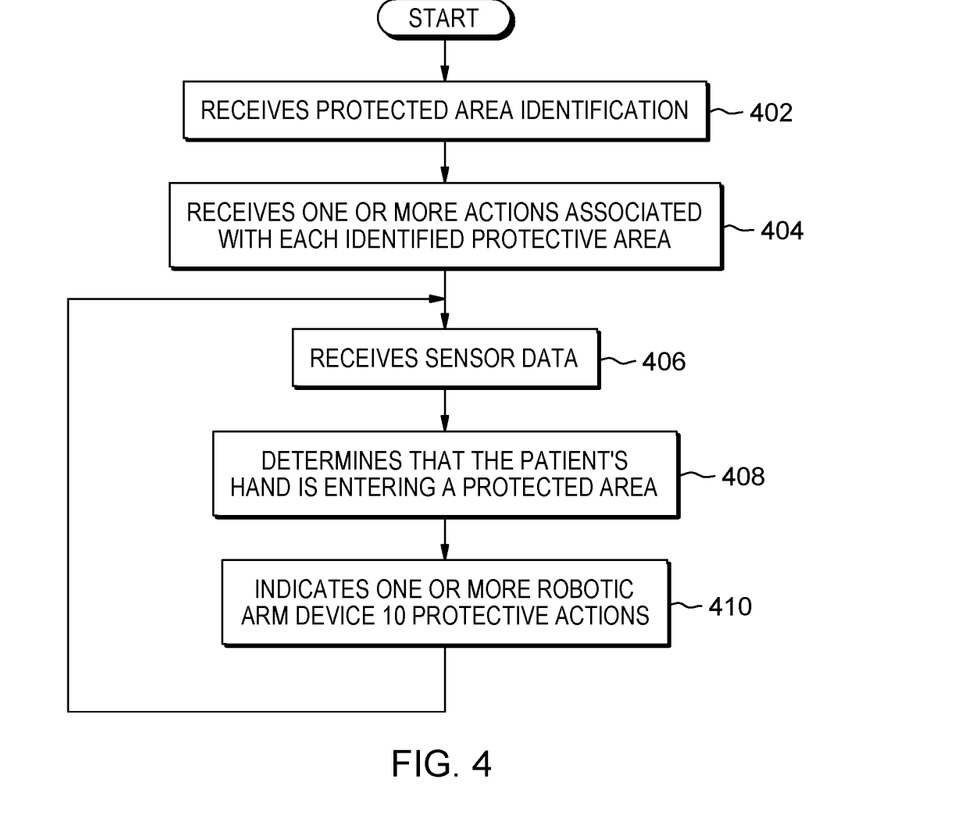
FIG. 4 is a flow chart diagram depicting operational steps for the patient protective program in the robotic arm device, in accordance with at least one embodiment of the invention.

FIG. 4 is a flow chart diagram depicting operational steps for PPP 12 in robotic arm device 10, in accordance with at least one embodiment of the invention. In step 402, PPP 12 receives protected area identification from AR glasses 2. In various embodiments, PPP 12 receives data from PPA 3 in AR glasses 2 identifying one or more protected areas associated with the patient as depicted and previously discussed with respect to FIG. 1. For example, PPP 12 may receive digital video data, or a digital image data collected by sensors 4 in AR glasses 2 to identify a protected area such as the face of the patient or an identification of a joint such as an elbow to have a limited range of motion. In some embodiments, PPP 12 receives from PPA 3 a shape of the protected area (e.g., a three-dimensional spherical area, a dome, a cubic area, a two-dimensional area, etc.).

In some cases, for example when RF tags using NFC are placed by a medical professional on one or more of the patient, on the patient's hospital gown, attached to robotic arm device 10 adjacent to a protected area, or on a hospital bed adjacent to a protected area of the patient, the protected area identification may be a distance such as 5 cm from the RF tag placed on the patient's hospital gown above surgical stitches or placed on an IV tube connection to the patient. Similarly, one or more of sensors 15 in robotic arm device 10 are digital cameras attached the patient's wrist or with robotic arm device 10 finger extensions (not depicted in FIG. 3), the protected area can be a distance from an identified feature such as the patient's eyes identified to PPP 12 by an input to UI 14 by the medical professional. In some embodiments, PPP 12 receives from PPA 3 in AR glasses 2 gaze detection data including a direction and/or a distance from a patient location viewed by the medical professional that is input, by the medical professional wearing AR glasses 2, as a protected area.

In step 404, PPP 12 receives one or more actions associated with each identified protective area. In various embodiments, PPP 12 receives instructions or commands for one or more actions by robotic arm device 10 for each protected area from a medical professional wearing AR glasses 2. For example, PPP 12 may receive, from a medical professional wearing AR glasses 2, an instruction for robotic arm device 10 to prevent a patient, who just completed elbow surgery, from bending their elbow more than 20 degrees. In this example, the patient's elbow is a protected area and robotic arm device 10 can use hinge 27 (depicted in FIG. 2) to prevent over bending of the elbow. In another example, PPP 12 may receive from a computer or smart phone of a physical therapist instructions for robotic arm device 10 to initiate an action of the patient to lift their arm 30 degrees from horizontal every 3 hours for a patient recovering from shoulder surgery (e.g., to prevent a frozen shoulder).

In yet another example, PPP 12 may receive instructions from the medical professional for one patient identifying when this patient is sleeping using sensors 15 to prevent contact with the patient's face area using robotic arm device 10. However, PPP 12 in a robotic arm device 10 worn by a different patient may receive instructions from the doctor to allow this second patient facial contact during sleep. In some embodiments, upon determining that the patient is asleep using sensor data and known sleep detection methods, PPP 12 sends instructions to robotic arm device 10 to prevent the patient from moving their hand into a protected area. In this way, PPP ensures that a sleeping patient does not accidently cause harm to a protected area by an uncontrolled movement during sleep. Additionally, upon determining that the patient is awake, PPP 12 based at least in part, on received input from AR glasses 2 of the medical professional, sends instructions to robotic arm device 10 to allow the patient to move their hands toward a protected area while increasing the resistance of robotic arm device 10 to movement toward the protected area. When robotic arm device 10 increases the resistance to the patient's movement toward a protected area, the patient must use additional force to move their hand into the protected area. The increasing resistance to the patient's movements into the protected area helps the patient to understand areas where their hands and arms can move freely and serves as an alert to the patient of areas, such as the protected area, that should have limited to no contact.

Additionally, in various embodiments, PPP 12 receives, from AR glasses 2 or a computing device associated with the treating medical professional of the patient, one or more parameters associated with the patient and/or the patient's treatment plan. The parameters can include one or more actions specific to the patient and/or specific to the patient's treatment plan. In various embodiments, PPP 12 sends the received parameters along with any associated actions to be taken by robotic arm device 10 for each parameter. The received parameters can include one or more of the following: patient age specific parameters, patient disease specific parameters, patient surgery specific parameters (e.g., for shoulder surgery vs. knee replacement), recovery plan for the patient, patient state specific parameters (e.g., awake, asleep, unconscious, etc.), observed patient mood or attitude (e.g., agitated), and patient specific parameters associated with the proximity of medical staff to the patient. For example, patient age specific parameters provided by the medical staff are typically dependent on the patient's age and can be different for a young child who is four years old, an infant, or an older child who is a teenager. The parameters provided by the doctor to PPP 12 for robotic arm device 10 when the patient is an infant includes instructions for robotic arm device 10 to prevent entry into a protected area while the instructions for PPP 12 and robotic arm device 10 when the patient is a teenage are to initiate an audible alert for the teenager when PPP 12 determines the patient's hand is nearing a protected area. Similarly, patient surgery specific parameters received by PPP 12 for robotic arm device 10 for a patient who received rotator cuff repair surgery may include instructions for robotic arm device 10 to move the patient's shoulder ten centimeters every four hours for a week post-surgery.

In some cases, the instructions for actions by robotic arm device 10 that are received by PPP 12 with the medical professional's parameters. For example, the received patient specific parameters associated with the proximity of medical staff to the patient for one patient may include instructions for robotic arm device 10 to allow unrestricted movement by the patient when PPP 12 determines, from sensor data, that a nurse, doctor, or other medical professional is near the patient (e.g., less than fifteen meters away from the patient). The proximity of a medical staff can be determined, for example, based on PPP 12 received sensor 15 data such as NFC/proximity detection data or video detection of nearby medical staff. In another example, the patient specific parameters associated with the proximity of medical staff to the patient for another patient in intensive care may include instructions to robotic arm device 10 to prevent the patient from touching their oxygen mask area unless a medical professional is within five meters.

In step 406, PPP 12 receives sensor data from sensors 15 in robotic arm device 10. For example, PPP 12 may receive accelerometer data from sensor 15 attached to the patient's wrist indicating that a patient with a two-directional hinged robotic arm device 10 is quickly moving their hand in an upward direction. In another example, PPP 12 may receive digital video data from one of sensors 15 that is a video camera positioned under the patient's wrist or attached to a finger extension of robotic arm device 10 indicates that the patient is moving into a protected area. In yet another example, PPP 12 receives sensor data from sensors 15 associated with an elbow hinge in robotic arm device 10 indicating the patient is exhibiting a fifty degree a range of motion for his or her elbow in robotic arm device 10.

In step 408, PPP 12 determines that the patient's hand is entering a protected area associated with the patient based, at least in part, on received sensor data from one or more of sensors 15. For example, using known digital video or digital image analysis, PPP 12 determines that the patient's hand is approaching the patient's eyes and is about to enter a protected area around the patient's eyes. In another example, using known methods of near-field communication (NFC) and sensor data from sensors 15 (e.g., an RF receiver) in robotic arm device 10, PPP 12 determines that the patient's hand is in a protected area such as a surgical area marked by RF tags attached to the patient or to the patient's hospital gown.

In step 410, PPP 12 initiates one or more robotic arm device 10 actions associated with a protected area. Upon determining that the patient's hand, arm, shoulder, or fingers are entering a protected area, PPP 12 sends instructions to robotic arm device 10 to execute at least one action, input by a medical professional, that is associated with the protected area. For example, when PPP 12 receives instructions, from a computing device (e.g., AR glasses 2) associated with a medical professional responsible for the patient, to prevent the patient from contacting their face then, when PPP 12 determines that the patient's fingers are in close proximity to their face, robotic arm device 10, PPP 12 increases resistance to the patient's hand movement toward their face or locks the hinging mechanism in robotic are device 10 to prevent facial contact. In another example of an action or instruction from a medical professional to robotic arm device 10 that is provided by PPP 12 to robotic arm device 10 to prevent facial contact by the patient could be a ringing alarm sounded by an audio device in UI 14 or in one of sensors 15. In some cases, instructions for both an audible alarm such as a ringing alarm and resistance to patient's movement toward their face can be received by PPP 12 from the medical professional using AR glasses 2. In one embodiment, PPP 12, responsive to determining that the patient's hand is moving into a protected area, provides instructions to robotic arm device 10 to either verbally instruct the patient to clean their hands, for example, using cleaning station 35 in FIG. 3 or to initiate UV light 28 in FIG. 2 to remove potential pathogens from the patient's hands.

Figure 5:
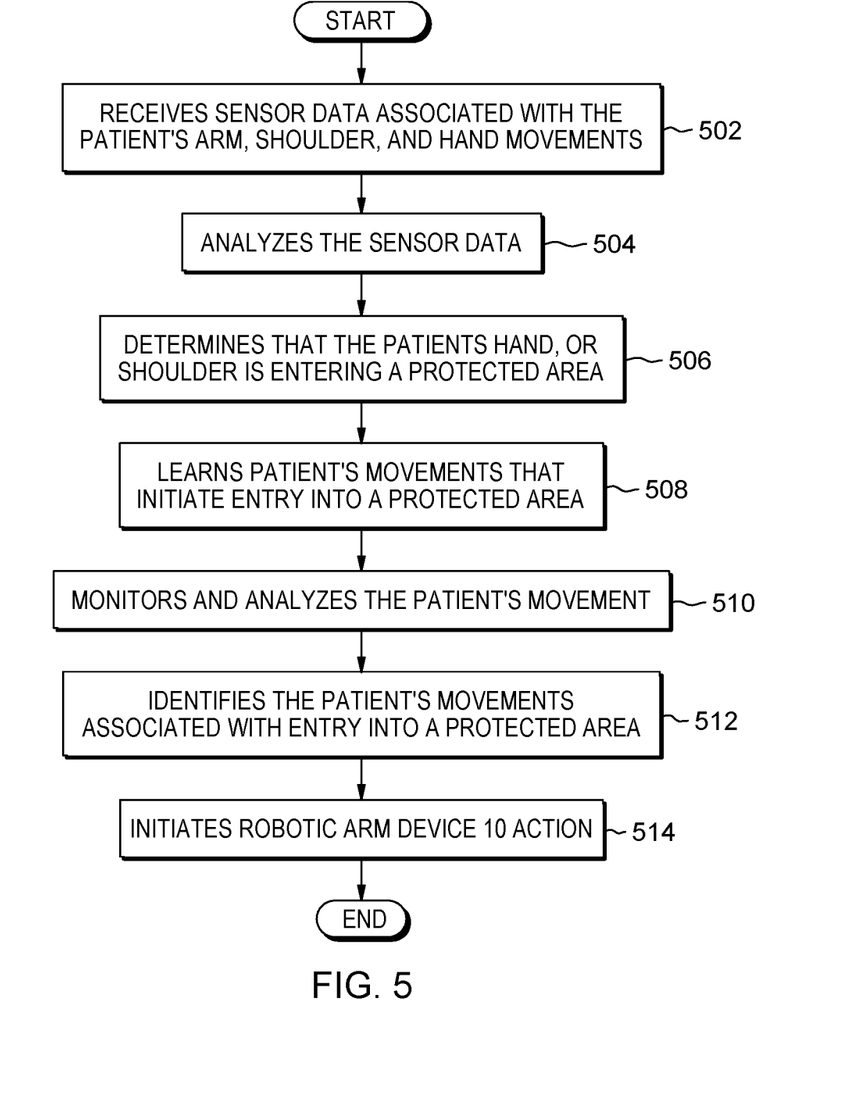
FIG. 5 is a flow chart diagram depicting operational steps for the patient protective program in the robotic arm device using machine learning to anticipate patient's movements, in accordance with at least one embodiment of the invention.

FIG. 5 is a flow chart diagram depicting operational steps for PPP 12 in robotic arm device 10 using machine learning to anticipate the patient's movements, in accordance with at least one embodiment of the invention. After receiving protected area identification and instructions for actions associated with each protected area as previously discussed with respect to steps 402 and 404 of FIG. 4, in step 502, PPP 12 receives, from sensors 15, sensor data associated with the patient's hand, arm, and shoulder movements. As previously discussed, sensors 15 may include accelerometers, compass chips, gyroscopic chips such as gyroscopes used in micro-electro-mechanical systems (MEMS), small digital cameras, etc. that can be used to record patient's hand, finger, arm, and shoulder movements. In various embodiments, sensors 15 send the sensor data associated with the patient's movements to PPP 12. In some cases, PPP 12 may retrieve sensor data from sensors 15 at pre-determined times such as every 15 minutes. PPP 12 may send the sensor data to storage 13 in computer 11.

In step 504, PPP 12 analyzes the data relating to the patient's arm, shoulder, and hand movements. Using known machine learning algorithms along with received sensor data on the patient's movements over time, PPP 12 analyzes the received sensor data associated with movements of the patient. For example, during analysis of the received sensor data associated with the patient's movements, PPP 12 may determine one or more of a frequency of specific patient motions (e.g., how often a motion occurs), an order of various motions, the direction of patient movement, the speed of the patient's movement, the acceleration of the patient's hand, fingers, or arms, a proximity of the patient's hand, fingers, shoulder, and/or arm to the protected area. PPP 12 analyzes the patient's movement with respect to one or more protected areas (e.g., does a movement go away from or into a protected area).

In step 506, PPP 12 determines that one or more of the patient's hand, fingers, or arm is entering a protected area. Using any of the techniques discussed above with reference to step 408 of FIG. 4, PPP 12 determines that the patient's arm, hand, or fingers are entering a protected area. For example, using received video data captured by sensors 15 (e.g., a video camera in robotic arm device 10 attached to the patient's wrist), PPP 12 analyzes the captured video to determine that the patient's hand is approaching a protected area above the patient's IV tube attachment area. In another example, an RF receiver in robotic arm device 10 determines that the patient's hand is entering a protected area identified by an RF tag (e.g., in the patient's hospital gown, in the patient's face mask, embedded in the IV tube, or on the patient).

In step 508, PPP 12 learns the patient's movements that initiate entry into a protected area. PPP 12 retrieves historical sensor data on various patient movements when the patient is wearing robotic arm device 10 (e.g., hand, finger, arm, or shoulder movements). Using known machine learning algorithms, for example, in conjunction with the recently received sensor data, the historical sensor data on the patient's movement's, and known human motion studies, PPP 12 learns to predict which movements of the patient's hand, fingers, shoulders, and/or arm typically proceed entry into a protected area of the patient.

In step 510, PPP 12 monitors and analyzes the patient's movements with respect to each protected area. PPP 12 receives in near real-time the sensor data from sensor 15 in robotic arm device 10 that is associated with the patient's hand, finger, arm, and shoulder movements in robotic arm device 10, and analyzes each patient movement with respect to each nearby protected area.

In step 512, PPP 12 identifies that the patient's movements are associated with entry into a protected area. Using the learned patient movement's in step 508 that typically proceed entry into each protected area, PPP 12 determines when the patient is most likely to enter a protected area with their hands, fingers, arms, or shoulders. In various embodiments PPP 12 determines that the patient's hand is entering a protected area based, at least in part, on the near real-time or most current sensor data. PPP 12 using the received historical and near real-time sensor data with the machine learning algorithms predicts which movement of the patient's hand, fingers, shoulders, and/or arms typically proceed entry into a protected area of the patient. In various embodiments, PPP 12 identifies when the patient's hand, finger, arm, or shoulder movements are most likely to be associated with entry into a protected area.

In step 514, PPP 12 initiates one or more robotic arm device 10 actions associated with one of the patient's protected areas, for example, to prevent entry into one of the patient's protected areas Using one or more of the actions discussed in detail with respect to step 410 of FIG. 4, PPP 12 sends instructions to robotic arm device 10 to prevent entry into a protected area. For example, PPP 12 may send an instruction to robotic arm device 10 to increase resistance in a hinge to discourage patient movement into a protected area. In an embodiment, PPP 12 ends after providing an instruction. In various embodiments, PPP 12, after initiating at least one robotic arm device 10 action, returns to step 510 and continues to monitor and analyze the patient's movements.

Figure 6:
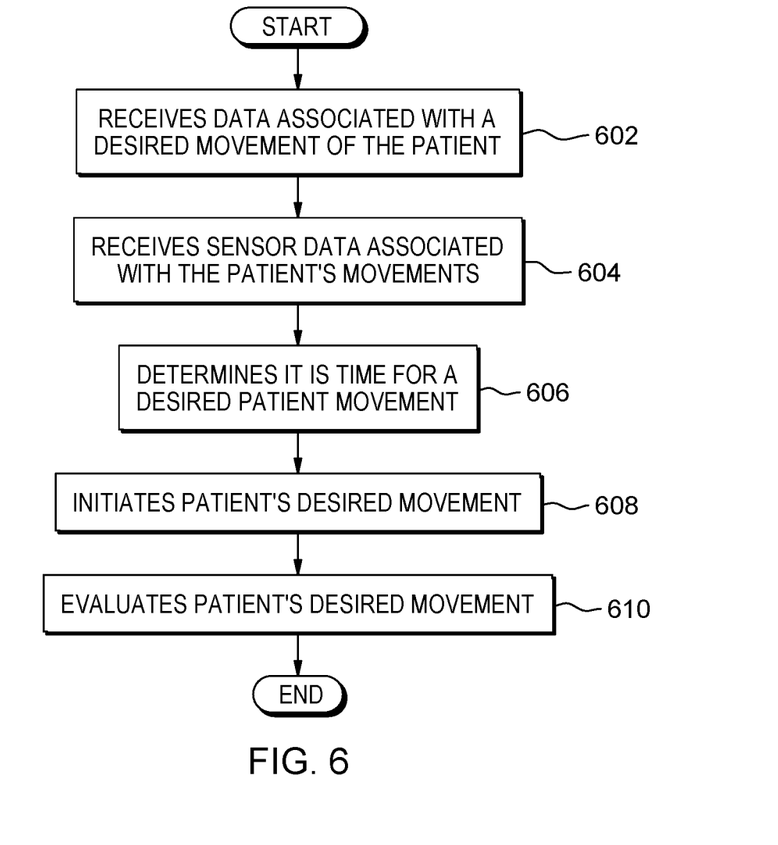
FIG. 6 is a flow chart diagram depicting operational steps for the patient protective program in the robotic arm device to initiate desired patient movements, in accordance with at least one embodiment of the invention.

FIG. 6 is a flow chart diagram depicting operational steps for PPP 12 in robotic arm device 10 to initiate desired patient movements, in accordance with at least one embodiment of the invention. In some cases, it is desirable for a patient to move a shoulder, arm, wrist, fingers, or thumb after some surgeries or injuries. In these cases, PPP 12 can provide patients assistance in regularly moving the desired limb or muscles on a pre-determined schedule, as directed by a medical professional or physical therapist. PPP 12 can monitor a patient's movements to limit or increase a range of motion or a resistance to a motion. In some cases, PPP 12 provides instructions to robotic arm device 10 for an alert such as a vibration indicating to the patient that it is time to exercise or move a specific joint or muscle.

In step 602, PPP 12 receives sensor data associated with a desired movement of the patient. In some cases, specified patient movements or physical therapy are prescribed by a physical therapist assigned to the patient. In these cases, one or more desired patient movements may be instructed to PPP 12. The instructions may include a frequency of performing the desired movement, a request to monitor or measure the patient's movements, and how to perform the desired movement.

In some embodiments, the desired patient movement is captured by sensors 15 of robotic arm device 10 when a medical professional or physical therapist temporarily wears robotic arm device 10 and indicates, for example, on UI 14, a demonstration of a desired movement is occurring. Sensors 15 in robotic arm device 10 capture the desired motion (e.g., a speed, direction of motion using compass chips, hinge action, etc.) as demonstrated by the medical professional and stores the information on the desired movement (e.g., angle of motion, range of motion, speed of motion, etc.) in storage 13 of robotic arm device 10. In this case, after demonstrating the desired motion to robotic arm device 10, the medical professional re-attaches robotic arm device 10 to the patient. In some cases, the medical professional enters a command on UI 14 for PPP 12 to retrieve the captured sensor data of the desired motion.

In other embodiments, a medical professional wearing AR glasses 2 demonstrates the desired movement which is captured as a video by sensors 4 in AR glasses 2 that is sent to one of PPA 3 in AR glasses 2 or directly to PPP 12 in response to a command by the medical professional on UI 5 in AR glasses 2. In other cases, the medical professional may input directions for the desired patient movement verbally or by text into a UI of their computer device or smart phone and sends the instructions to PPP 12 for an audio replay or display on UI 14 of robotic arm device 10 to the patient. In some cases, PPP 12 sends instructions or a command to robotic arm device 10 to perform the desired patient movement. For example, PPP 12 may receive from a computer or smart phone of a physical therapist instructions for robotic arm device 10 for the patient to lift their arm 30 degrees from horizontal every 3 hours for a patient recovering from shoulder surgery (e.g., to prevent a frozen shoulder).

In step 604, PPP 12 receives sensor 15 data associated with the patient's movements associated with performing the desired patient movement. In some embodiments, PPP 12 receives data from sensors 15 in robotic arm device 10 attached to the patient. The received data from sensors 15 can include sensor data associated with a patient's injured or operated on limb, digit, or muscle including speed of limb movement, muscle movement, digital video, the number of desired actions performed, a time stamp of the performed desired action, acceleration of a limb, or other similar sensor data associated with the patient performing the desired movement.

In step 606, PPP 12 monitors the time. For example, using a clock chip in computer 11 or in robotic arm device 10, PPP 12 monitors a time of day or a time passed since the last movement of robotic arm device 10 associated with the desired movement of the patient's shoulder, arm, thumbs, or finger. In some embodiments, PPP 12 includes a schedule of movements input by a medical professional responsible for the patient's care. The schedule in PPP 12 can include a timetable for changes to the desired patient's movements. For example, to prevent a frozen shoulder after shoulder surgery PPP 12 includes instructions for robotic arm device 10 to provide one of a verbal alert or a reminder to the patient to move their shoulder by ten degrees every four hours for the first month post-surgery. PPP 12 can record a time when the desired movement is performed and can, for example, using a clock chip monitors a time from the last desired movement captured by sensors 15 in robotic arm device 10.

In step 606, PPP 12 determines it is time for the desired patient movement. For example, using the clock chip in robotic arm device 10, PPP 12 identifies that it is time for a desired patient movement. In various embodiments, PPP 12 receives both the desired patient movement and a time or timetable for performing the patient movement from one of UI 14 or from a computing device such as a tablet of the medical professional providing a treatment plan for the patient.

In step 608, PPP 12 initiates the patient's desired movement. For example, PPP 12 can send a command to robotic arm device 10 to move the patient's elbow fifteen degrees every hour for the first 24 hours after surgery. In some cases, PPP 12 can send to UI 14 a command to provide an audible command or alert such as a bell to remind the patient to bend their elbow.

In step 610, PPP 12 evaluates the patient's desired movement. In various embodiments, PPP 12 receives sensor data associated with the desired movement of the patient. For example, PPP 12 receives sensor data on the range of motion of a joint or limb performing the desired movement, the speed of the desired movement performed by the patient, a direction of the movement, a resistance registered by sensor 15 in a hinge of robotic arm device 10, a limb acceleration, video, or other sensor data from sensors 15 in robotic arm device 10. In various embodiments, PPP 12 determines whether the received sensor data associated with the desired motion has attained a patient treatment plan goal. When PPP 12 determines based, at least in part, on the received sensor 15 associated with the desired patient movement that the desired patient movement attains the treatment plan goal then, PPP 12 moves to the next level of the patient treatment plan. For example, upon determining that the current treatment plan goal is attained, PPP 12 sends a command to robotic arm device 10 to increases one or more of a range of motion, frequency of the desired motion, a resistance to the desired motion, and/or sends a message to the patient's medical professional's device or to the medical professional on UI 14 that the patient has achieved the treatment plan goal. In some cases, upon achievement of the desired motion or a desired treatment plan, PPP 12 ends monitoring of the desired motion (e.g., according to pre-programmed instructions from the medical professional) and the program ends.

In other cases, PPP 12 may determine that the patient is not following the treatment plan or is not progressing (e.g., not extending the range of motion or making the desired speed of motion) and sends a message to UI 14 for the patient to view or in other cases, sends a message to the medical professional monitoring the patient's care. In this case, PPP 12 alerts the medical professional that the desired patient progress or treatment plan progression is not occurring on schedule.

Figure 7:
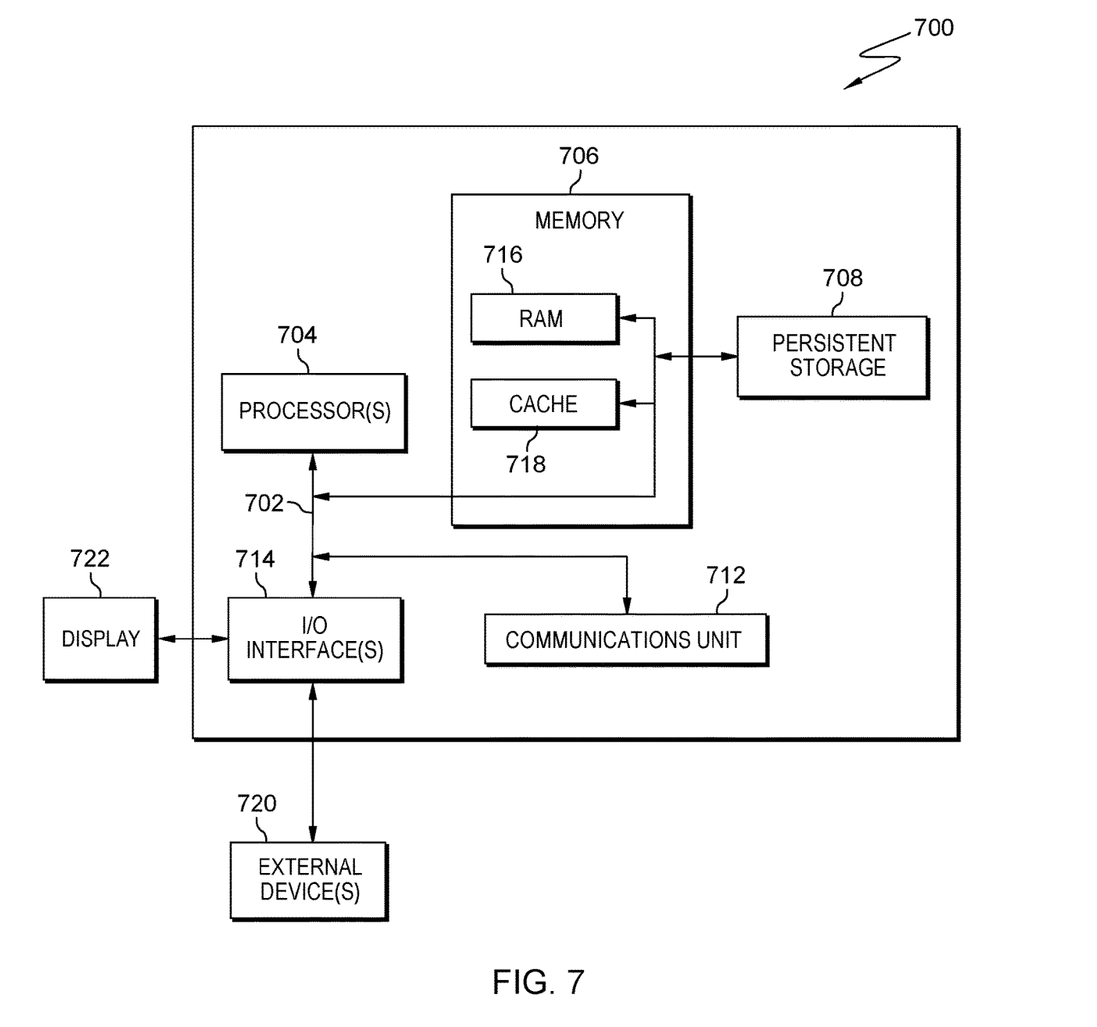
FIG. 7 is a block diagram depicting components of a computer system suitable for executing the patient protective program, in accordance with at least one embodiment of the invention.

FIG. 7 is a block diagram depicting components of a computer system suitable for executing PPP 12 in robotic arm device 10, in accordance with at least one embodiment of the invention. FIG. 7 displays the computer system 700, one or more processor(s) 704 (including one or more computer processors or central processor units), a communications fabric 702, a memory 706 including, a RAM 716, and a cache 718, a persistent storage 708, a communications unit 712, I/O interfaces 714, a display 722, and external devices 720. It should be appreciated that FIG. 7 provides only an illustration of one embodiment and does not imply any limitations with regard to the environments in which different embodiments may be implemented. Many modifications to the depicted environment may be made.

As depicted, the computer system 700 operates over the communications fabric 702, which provides communications between the computer processor(s) 704, memory 706, persistent storage 708, communications unit 712, and input/output (I/O) interface(s) 714. The communications fabric 702 may be implemented with an architecture suitable for passing data or control information between the processors 704 (e.g., microprocessors, communications processors, and network processors), the memory 706, the external devices 720, and any other hardware components within a system. For example, the communications fabric 702 may be implemented with one or more buses.

The memory 706 and persistent storage 708 are computer readable storage media. In the depicted embodiment, the memory 706 comprises a random-access memory (RAM) 716 and a cache 718. In general, the memory 706 may comprise any suitable volatile or non-volatile one or more computer readable storage media.

Program instructions for PPP 12 may be stored in the persistent storage 708, or more generally, any computer readable storage media, for execution by one or more of the respective computer processors 704 via one or more memories of the memory 706. In an embodiment, program instructions for PPP 12 may be stored in memory 706. The persistent storage 708 may be a magnetic hard disk drive, a solid-state disk drive, a semiconductor storage device, read only memory (ROM), electronically erasable programmable read-only memory (EEPROM), flash memory, or any other computer readable storage media that is capable of storing program instruction or digital information.

The media used by the persistent storage 708 may also be removable. For example, a removable hard drive may be used for persistent storage 708. Other examples include optical and magnetic disks, thumb drives, and smart cards that are inserted into a drive for transfer onto another computer readable storage medium that is also part of the persistent storage 708.

The communications unit 712, in these examples, provides for communications with other data processing systems or devices. In these examples, the communications unit 712 may comprise one or more network interface cards. The communications unit 712 may provide communications through the use of either or both physical and wireless communications links. In the context of some embodiments of the present invention, the source of the various input data may be physically remote to the computer system 700 such that the input data may be received, and the output similarly transmitted via the communications unit 712.

The I/O interface(s) 714 allow for input and output of data with other devices that may operate in conjunction with the computer system 700. For example, the I/O interface 714 may provide a connection to the external devices 720, which may be as a keyboard, keypad, a touch screen, or other suitable input devices. External devices 720 may also include portable computer readable storage media, for example thumb drives, portable optical or magnetic disks, and memory cards. Software and data used to practice embodiments of the present invention may be stored on such portable computer readable storage media and may be loaded onto the persistent storage 708 via the I/O interface(s) 714. The I/O interface(s) 714 may similarly connect to a display 722. The display 722 provides a mechanism to display data to a user and may be, for example, a computer monitor.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disk read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adaptor card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, though the Internet using an Internet Service Provider). In some embodiments, electronic circuitry including, for example programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram blocks or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of computer program instructions, which comprises one or more executable instructions for implementing the specified logical function(s). In some alternative implementations, the functions noted in the block may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method of a program in a robotic arm device attached to a user, the computer-implemented method comprising:
   receiving, by one or more computer processors, data identifying at least one protected area of the user, wherein the data includes an identification of at least one radio frequency device adjacent to each of the at least one protected area of the user;
   receiving, by the one or more computer processors, instructions for a treatment plan with one or more actions by the robotic arm device associated with the at least one protected area of the user;
   initiating, by the one or more computer processors, an action of the one or more actions by the robotic arm device associated with the least one protected area of the user;
   receiving, by the one or more computer processors, sensor data from the at least one radio frequency device associated with the action of the one or more actions by the robotic arm device from one or more sensors in the robotic arm device; and
   evaluating, by the one of more computers, the sensor data associated with the action of the one or more actions by the robotic arm device to determine if the action of the one or more actions attains a treatment plan goal.

2. A computer-implemented method of claim 1, wherein the data identifying the at least one protected area of the user includes receiving data from one of a radio frequency tag adjacent to the one or more protected areas or a radio frequency receiver adjacent to the one or more protected areas.

3. A computer-implemented method of claim 1, wherein receiving instructions for the one or more actions by the robotic arm device associated with the least one protected area of the user includes instructions to the robotic arm device for an increasing resistance to movement of the patient toward the at least one protected area.

4. A computer-implemented method of claim 1, wherein receiving the instructions for the one or more actions by the robotic arm device associated with the least one protected area of the user include instructions, further comprises receiving, by the one or more computer processors, instructions for the robotic arm device to generate a vibration indicating a time for an action by the user wearing the robotic arm device, wherein the action is one of the one or more actions by the robotic arm device associated with the at least one protected area of the user.

5. A computer-implemented method of claim 1, wherein the instructions for the one or more actions by the robotic arm device associated with the least one protected area of the user, further comprises receiving, by the one or more computer processors, instructions associated with at least one action of one or more actions of a second user wearing the robotic arm device.

6. A computer-implemented method of claim 3, wherein the instructions for the one or more actions by the robotic arm device associated with the least one protected area of the user, further comprise include instructions, by the one or more computer processors, to initiate by robotic arm device worn by the user a performance of the at least one action of the one or more actions of the second user wearing the robotic arm device.

7. A computer-implemented method of claim 1, wherein the robotic arm device is attached to an arm of the user, to an elbow of the user, to a wrist of the user, and extends to a shoulder of the user.

8. A computer program product in a robotic arm device attached to a patient, the computer program product comprising:
   one or more computer readable storage media and program instructions stored on the one or more computer readable storage media, the program instructions executable by a processor, the program instructions comprising instructions for:
   receiving, by one or more computer processors, data identifying at least one protected area of the user, wherein the data includes an identification of at least one radio frequency device adjacent to each of the at least one protected area of the user;
   receiving, by the one or more computer processors, instructions for a treatment plan with one or more actions by the robotic arm device associated with the at least one protected area of the user;
   initiating, by the one or more computer processors, an action of the one or more actions by the robotic arm device associated with the least one protected area of the user;
   receiving, by the one or more computer processors, sensor data from the at least one radio frequency device associated with the action of the one or more actions by the robotic arm device from one or more sensors in the robotic arm device; and
   evaluating, by the one of more computers, the sensor data associated with the action of the one or more actions by the robotic arm device to determine if the action of the one or more actions attains a treatment plan goal.

9. The computer program product of claim 8, wherein the data identifying the at least one protected area of the user includes receiving data from one of a radio frequency tag adjacent to the one or more protected areas or a radio frequency transmitter adjacent to the one or more protected areas.

10. The computer program product of claim 8, wherein instructions for the one or more actions by the robotic arm device associated with the least one protected area of the user includes instructions to the robotic arm device for an audible alarm upon entering the at least one protected area.

11. The computer program product of claim 8, wherein instructions for the one or more actions by the robotic arm device associated with the least one protected area of the user, further comprises receiving, by the one or more computer processors, instructions for the robotic arm device to generate a vibration indicating a time for an action by the user wearing the robotic arm device, wherein the action is one of the one or more actions by the robotic arm device associated with the at least one protected area of the user.

12. The computer program product of claim 8, wherein instructions for the one or more actions by the robotic arm device associated with the least one protected area of the user, further comprises receiving, by the one or more computer processors, instructions associated with at least one action of one or more actions of a second user wearing the robotic arm device.

13. The computer program product of claim 12, wherein instructions for the one or more actions by the robotic arm device associated with the least one protected area of the user, further comprise instructions, by the one or more computer processors, to initiate by robotic arm device worn by the user to perform the at least one action of the one or more actions of the second user wearing the robotic arm device.

14. The method of claim 5, wherein receiving instructions for the one or more actions by the robotic arm device associated with the at least one protected area of the user, further comprises receiving, by the one or more computer processors, sensor data associated with the at least one action of the one or more actions of the second user wearing the robotic arm device is for a demonstration of a desired motion of the robotic arm device.

15. The method of claim 14, further comprising:
receiving, by the one or more computer processors, instructions from the second user to store the sensor data associated with the least one action of the one or more actions of the second user wearing the robotic arm device, wherein the at least one action of the one or more actions is associated with the treatment plan goal;
receiving, by the one or more computer processors, instructions from the second user to retrieve the sensor data associated with the at least one action of the one or more actions by the second user wearing the robotic arm device;
initiating, by the one or more computer processors, the at least one action of the one or more action by the second user wearing the robotic arm device when the user is wearing the robotic arm device; and
receiving, by the one or more computer processors, sensor data associated with the robotic arm device worn by the user performing the at least one action of the one or more actions for a determination of whether the sensor data indicates the attainment of the treatment plan goal.

16. The method of claim 1, responsive to determining that the action of the one or more actions does attain the treatment plan goal, initiating, by the one or more computer processors, a next level of the treatment plan.

17. The method of claim 1, responsive to determining that the action of the one or more actions does not attain the treatment plan goal, sending, by the one or more computer processors, to a user interface of the robotic arm device, a message to display to the user that user is not meeting a desired speed of motion for the action.

18. The method of claim 1, responsive to determining that the action of the one or more actions does not attain the treatment plan goal, sending, by the one or more computer processors, to a computing device associated with a medical professional responsible for treatment of the user, a message to display to the medical professionally that the user is not meeting a desired speed of motion for the action.

\* \* \* \* \*